(12) United States Patent
Hayward et al.

(10) Patent No.: US 8,329,310 B2
(45) Date of Patent: Dec. 11, 2012

(54) INSECTICIDAL COMPOSITION AND METHOD

(75) Inventors: Peter James Hayward, New Plymouth (NZ); Christopher Molloy, New Plymouth (NZ); Wallace James Rae, New Plymouth (NZ); Andre Frederick Siraa, New Plymouth (NZ)

(73) Assignee: Zelam Limited (NZ)

( * ) Notice: Subject to any disclaimer, the term of this patent is extended or adjusted under 35 U.S.C. 154(b) by 0 days.

(21) Appl. No.: 13/256,298

(22) PCT Filed: Mar. 25, 2010

(86) PCT No.: PCT/NZ2010/000057
§ 371 (c)(1),
(2), (4) Date: Sep. 13, 2011

(87) PCT Pub. No.: WO2010/120192
PCT Pub. Date: Oct. 21, 2010

(65) Prior Publication Data
US 2012/0003491 A1    Jan. 5, 2012

(30) Foreign Application Priority Data
Apr. 17, 2009 (NZ) ......................... 576293

(51) Int. Cl.
*B32B 23/04* (2006.01)
(52) U.S. Cl. ................. 428/532; 428/536; 428/537.1
(58) Field of Classification Search ............ 428/532, 428/536, 537.1
See application file for complete search history.

(56) References Cited

U.S. PATENT DOCUMENTS

| 5,972,971 | A | 10/1999 | Heuer et al. | |
|---|---|---|---|---|
| 6,022,881 | A | 2/2000 | Asai et al. | |
| 6,077,863 | A * | 6/2000 | Reid et al. | 514/428 |
| 6,423,730 | B1 * | 7/2002 | Smith et al. | 514/365 |
| 2009/0318393 | A1 | 12/2009 | Shalaby | |
| 2010/0015194 | A1 | 1/2010 | Donath et al. | |

FOREIGN PATENT DOCUMENTS

| EP | 0895839 | * | 9/2006 |
|---|---|---|---|
| EP | 0895839 B1 | | 9/2006 |
| JP | 10007502 A | | 1/1998 |
| JP | 10203902 A | | 8/1998 |
| JP | 11207706 A | | 8/1999 |
| JP | 2000080005 A | | 3/2000 |
| JP | 2009-161471 A | | 7/2009 |
| WO | WO01/00256 A1 | | 4/2001 |
| WO | WO01/26456 | * | 4/2001 |
| WO | WO2007/106726 | * | 9/2007 |
| WO | WO2007/106726 A2 | | 9/2007 |
| WO | WO2007/123855 | * | 11/2007 |
| WO | WO2007/123855 A2 | | 11/2007 |
| WO | WO2008/079384 | * | 7/2008 |
| WO | WO2008/079384 A1 | | 7/2008 |
| WO | WO2009/129587 A1 | | 10/2009 |
| WO | WO2010/021687 A1 | | 2/2010 |

OTHER PUBLICATIONS

The International Search Report for PCT application PCT/NZ2010/000057 dated Jun. 9, 2010.

* cited by examiner

*Primary Examiner* — Leszek Kiliman
(74) *Attorney, Agent, or Firm* — Garcia-Zamor IP Law; Ruy M. Garcia-Zamor

(57) ABSTRACT

A composition for surface treatment of timber and wood products that provides protection against insect damage to all surfaces without any need for a secondary insecticide treatment of one or more new, untreated surfaces generated by post-treatment processing operations including sawing, cutting, drilling, bevelling, planing, sanding and/or a combination thereof, comprising one or more non-repellent insecticides.

18 Claims, 1 Drawing Sheet

Photograph of untreated and treated timber after termite exposure. The photograph shows the blocks from Replicate 1 of Trial 2072: (L-R) untreated, imidacloprid 5.0 g/m3, imidacloprid 10.0 g/m3, imidacloprid 20.0 g/m3, bifenthrin 10.9 g/m3, solvent control.
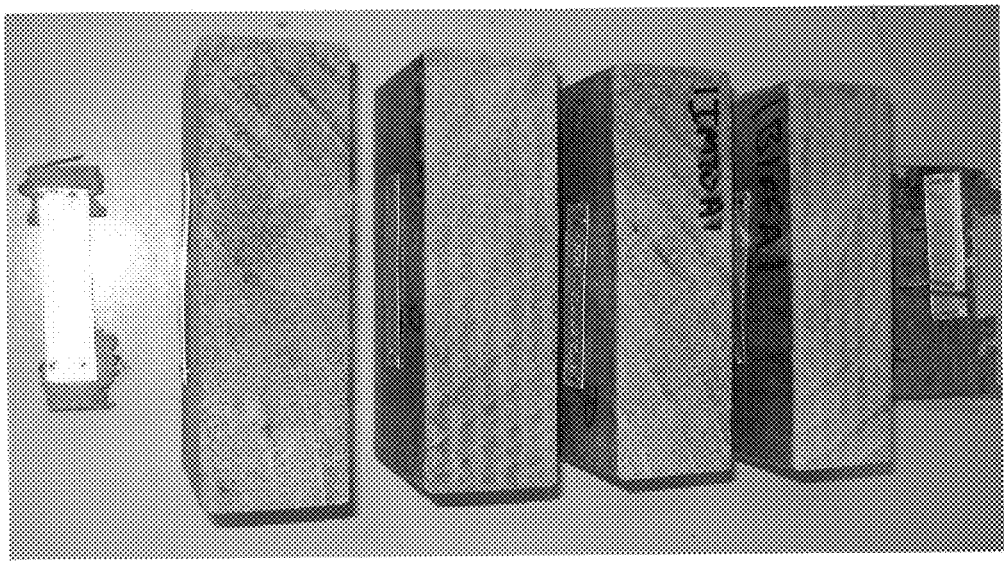

INSECTICIDAL COMPOSITION AND METHOD

CROSS REFERENCE TO RELATED APPLICATIONS

This application claims priority to the following patent applications: (1) Patent Cooperation Treaty Application PCT/NZ2010/000057 filed Mar. 25, 2010; and (2) New Zealand Patent Application No. NZ576293, filed on Apr. 17, 2009 each of the above cited applications is hereby incorporated by reference herein as if fully set forth in its entirety.

FIELD OF THE INVENTION

This invention relates to an insecticidal composition and its method of use for surface treatment of timber or wood products. More particularly, but not exclusively, the invention provides for the use of one or more non-repellent insecticides in the manufacture of an insecticidal composition, wherein said composition is to be used for surface treatment of timber or wood products. Even more particularly, the invention provides for the use of one or more non-repellent neonicotinoid insecticides in the manufacture of an insecticidal composition, wherein said composition is to be used for a single surface treatment of timber or wood products without the need for a secondary or subsequent insecticidal treatment.

BACKGROUND OF THE INVENTION

In the natural environment lignocellulosic materials in the form of forest litter and the like are rapidly broken down by mineralization and carbon cycling processes mediated by a host of insects and microorganisms. Many timber and wood-containing products, particularly those from softwood species, are also subject to insect damage as well as fungal degradation and discolouration. The most problematic insects are termites, ants, boring insects, weevils and various beetles. Timber and wood products may be protected against wood degrading organisms by the application of insecticides and fungicides.

Traditional methods of timber protection involve aqueous impregnation with inorganic preservatives such as copper chrome arsenic, sodium octaborate, alkaline copper quat ("ACQ") using vacuum and pressure, or the use of carbon-based preservatives in a solvent delivery system such as a light organic solvent preservative ("LOSP"). Both approaches produce high levels of active ingredient penetration but are expensive. Additionally the former method requires special care to avoid problems with dimensional stability and the latter method leaves solvent residues. Simpler and cheaper treatment options, generally suitable for lower hazard product applications such as enclosed building materials, include delivery of preservatives in the glues and resins used to make engineered wood products such as plywood and laminated veneer lumber and reconstituted wood products such as medium density fibreboard and the like. In the case of sawn timber or dimensional lumber, as well as wood products, surface treatment operations such as surface spraying or brief dipping procedures provide adequate protection, particularly against insect pests.

Most surface treatment operations are carried out in a sawmill or a wood processing mill and occur after the timber or wood product has been gauged, trimmed and cut to final dimensions, sanded etc. Post-treatment operations such as sawing, drilling etc, occur mainly on building sites or in a factory such as a frame and truss manufacturing facility where timber is sawn to produce framework such as trusses and other preassembled structures. These post-treatment operations expose new surfaces that have not been treated directly with insecticide. Accordingly, with surface-treated timber or wood products, it is industry practice to provide a secondary treatment operation in which the newly exposed surfaces are treated with insecticide before the structural members are nailed or otherwise fixed into place but this involves additional time, expense and risk to workers.

New generation insecticides including certain members of the neonicotinoid class of insecticides (for example imidacloprid, thiacloprid, dinotefuran, clothianidin and nitenpyram), phenylpyrazoles (for example fipronil and ethiprole), anthranilic diamide insecticides (for example rynaxypyr and flubendiamide), spinosyns (for example spinosad and spinetoram), chlorfenapyr and indoxacarb are not considered to have repellent activity toward insects that damage timber and wood products such as termites, ants, boring insects and the like.

These non-repellent insecticides are now the active ingredients of choice for eradication of collections of problematic ground-dwelling insects such as termite or ant colonies, because foraging members of the colony that encounter the insecticide (within an appropriate bait) are not repelled and instead are able to consume the insecticide, carry it back to the colony and spread the insecticide among other members of the colony before they die.

The prior art teaches that non-repellent insecticides used as a surface treatment for timber or wood products are unable to prevent insect damage to any untreated surfaces and that to avoid the need for secondary insecticide treatment of newly cut surfaces, for example on a building site, it is necessary to use surface treatment compositions and methods that utilise repellent insecticidal active ingredients. These compositions are both lethal to the target insects and repellent with respect to the target insects. This is based on prior art observations that untreated wood surfaces exposed after the initial surface treatment operation, for example the ends of sawn timber, provide a point of entry for insects unless an insecticide with repellent activity is present on neighbouring treated surfaces. Insecticides with repellent activity that may be used in surface treatments include synthetic pyrethroids such as permethrin, deltamethrin, cypermethrin and bifenthrin. Unfortunately these active ingredients have relatively high mammalian toxicities and workers handling products containing these active ingredients commonly experience paresthesia or skin irritation to varying extents.

OBJECT OF THE INVENTION

The object of the invention is to provide an improved composition and method for the treatment of timber and wood products that will obviate or minimise the disadvantages mentioned above, or which will at least provide the public with a useful choice.

SUMMARY OF THE INVENTION

Surprisingly, we have found that timber and wood products which have been surface-treated with non-repellent insecticides, then sawn to expose fresh untreated surfaces remain fully protected against insects such as termites without the need for a secondary insecticide treatment of the newly exposed surfaces. That is, non-repellent insecticides are used in a single treatment.

New generation non-repellent insecticides including non-repellent neonicotinoid insecticides and other aforementioned non-repellent insecticides have low mammalian toxicities, exhibit favourable environmental profiles and do not pose the risk of paresthesia or skin irritation to workers. In particular, the neonicotinoid insecticide imidacloprid is an insecticide with a very low mammalian toxicity, exhibits a favourable environmental profile and has a desirably high safety margin for exposed workers.

The ability to produce insect-resistant timber and wood products by surface treatment with non-repellent insecticides, without the need for a subsequent, secondary insecticide treatment of surfaces freshly sawn or otherwise exposed, as disclosed in this invention, means that builders and home handymen, for example, do not need to handle insecticides. This, coupled with the low toxicities of the abovementioned non-repellent insecticides delivers greater levels of safety over existing compositions, treatment methods, and treated timber and wood products.

The term "surface treatment" as used herein with reference to the composition and method of the invention means to apply or spread the composition onto any surface of a timber or wood product such that the composition coats or covers the surface. Generally, although not limited to, the method enables restricted penetration (0-10 mm, preferably 0-5 mm) below the treated surface of the timber or wood product, as opposed to a full treatment process that achieves complete sapwood penetration, usually by means of vacuum and pressure treatment, diffusion systems or relatively long soaking times. The terms "surface treatment" and similar terms are meant to embrace terms such as "exterior treatment", "envelope treatment", etc. Consequently, the terms are used interchangeably.

DESCRIPTION OF THE INVENTION

In a first broad aspect this invention provides a composition comprising one or more non-repellent insecticides when used as a surface treatment for timber and wood products that provides protection against insect damage to all surfaces without the need for a secondary insecticide treatment of one or more new, untreated surfaces generated by post-treatment processing operations including sawing, cutting, drilling, beveling, planing, sanding and/or a combination thereof.

Preferably, the non-repellent insecticide is selected from a non-repellent neonicotinoid, a phenylpyrazole, an anthranilic diamide insecticide, a spinosyn, chlorfenapyr and, indoxacarb.

Preferably, the non-repellent insecticide is a non-repellent neonicotinoid selected from the group comprising imidacloprid, thiacloprid, dinotefuran, clothianidin and nitenpyram.

Preferably the non-repellent neonicotinoid insecticide of the composition is imidacloprid.

Optionally, the composition may further comprise a penetration aid.

Optionally, the composition may further comprise one or more additional biocides.

Preferably, the composition is further characterised in being readily dispersed in aqueous or solvent-based systems or mixed water-solvent based systems.

In a second broad aspect this invention provides a method of timber or wood protection involving surface treatment of timber or wood products with an insecticidally effective amount of a composition containing one or more non-repellent insecticides as herein described.

In a third broad aspect the method provides protection against insect damage to all surfaces without the need for a secondary insecticide treatment of one or more new, untreated surfaces generated by post-treatment processing operations including sawing, cutting, drilling, beveling, planing, sanding and/or a combination thereof.

The method of the invention is further characterised in that no part of the one or more new, untreated surfaces generated by post-treatment processing operations is more than 50 mm from any neighbouring treated surface, and/or the combined area of the one or more new, untreated surfaces comprises less than 33% of the total surface area of the timber or wood product.

In a further broad aspect this invention provides for timber or wood products when treated according to the method of the invention.

DETAILED DESCRIPTION OF THE INVENTION

The preferred non-repellent neonicotinoid insecticides of the composition include:

imidacloprid (N-[1-[(6-chloro-3-pyridyl)methyl]-4,5-dihydroimidazol-2-yl]nitramide), thiacloprid ((3-((6-chloro-3-pyridinyl)methyl)-2-thiazolidinylidene)cyanamide), dinotefuran (1-methyl-2-nitro-3-(tetrahydro-3-furylmethyl)guanidine), clothianidin ((E)-1-(2-chloro-1,3-thiazol-5-ylmethyl)-3-methyl-2-nitroguanidine) and nitenpyram (1,1-ethenediamine, N-((6-chloro-3-pyridinyl)methyl)-N-ethyl-N'-methyl-).

The preferred phenylpyrazoles of the composition include:

fipronil (5-amino-1-(2,6-dichloro-$\alpha,\alpha,\alpha$-trifluoro-p-tolyl)-4-trifluoromethylsulfinylpyrazole-3-carbonitrile), and ethiprole (5-amino-1-(2,6-dichloro-$\alpha,\alpha,\alpha$-trifluoro-p-tolyl)-4-ethylsulfinylpyrazole-3-carbonitrile).

The preferred anthranilic diamide insecticides of the composition include:

rynaxypyr (3-bromo-4'-chloro-1-(3-chloro-2-pyridyl)-2'-methyl-6'-(methylcarbamoyl)pyrazole-5-carboxanilide, and flubendiamide (3-iodo-N'-(2-mesyl-1,1-dimethylethyl)-N-{4-[1,2,2,2-tetrafluoro-1-(trifluoromethyl)ethyl]-o-tolyl}phthalamide).

The preferred spinosyns of the composition include:

spinosad (mixture of (2R,3aS,5aR,5bS,9S,13S,14R,16aS,16bR)-2-(6-deoxy-2,3,4-tri-O-methyl-$\alpha$L-mannopyranosyloxy)-13-(4-dimethylamino-2,3,4,6-tetradeoxy-$\beta$-D-erythropyranosyloxy)-9-ethyl-2,3,3 a,5 a,5b,6,7,9,10,11,12,13,14,15,16a,16b-hexadecahydro-14-methyl-1H-as-indaceno[3,2-d]oxacyclododecine-7,15-dione and (2S,3 aR,5 aS,5bS,9S,13S,14R,16aS,16b5)-2-(6-deoxy-2,3,4-tri-O-methyl-$\alpha$-L-mannopyranosyloxy)-13-(4-dimethylamino-2,3,4,6-tetradeoxy-$\beta$-D-erythropyranosyloxy)-9-ethyl-2,3,3a,5 a,5b, 6,7,9,10,11,12,13,14,15,16a,16b-hexadecahydro-4,14-dimethyl-1H-as-indaceno[3,2-d]oxacyclododecine-7,15-dione), and spinetoram (mixture of 2R,3aR,5aR,5bS,9S,13S,14R,16aS,16bR)-2-(6-deoxy-3-O-ethyl-2,4-di-O-methyl-a-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7,15-dione) and (2R,3aR,5aS,5bS,9S,13S,14R,16aS,16b5)-2-(6-deoxy-3-O-ethyl-2,4-di-O-methyl-$\alpha$-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione).

Also preferred as non-repellent insecticides are:

chlorfenapyr (4-bromo-2-(4-chlorophenyl)-1-ethoxymethyl-5-trifluoromethyl-1H-pyrrole-3-carbonitrile), and indoxacarb (methyl(5)-N-[7-chloro-2,3,4a,5-tetrahydro-4a-(methoxycarbonyl)indeno[1,2-e][1,3,4]oxadiazin-2-yl-carbonyl]-4'-(trifluoromethoxy)carbanilate).

The composition preferably contains concentrations of non-repellent insecticide in the range 0.005% to 50% by weight at any stage of the process. Preferably the non-repellent insecticide is present at a concentration of 0.01% to 25% by weight of the total weight of the composition.

Suitable penetration aids include surfactants, wetting agents, oils, alcohols, glycols, glycol ethers, esters, amines, alkanolamines, quaternary ammonium compounds, amine oxides, triglycerides, fatty acid esters, fatty acid ethers, N-methyl pyrrolidone, dimethylformamide, dimethylacetamide, or dimethyl sulfoxide, and the like, as known in the art.

Suitable additional biocides include insecticides with repellent activity, fungicides, bactericides, mouldicides, algaecides, etc.

Further optional additives include insecticidal synergists, pigments, visible or invisible treatment markers, water repellents, fire retardants, anti-bloom agents and the like, as known in the art.

The composition is further characterised in being readily dispersed in aqueous or non-aqueous solvent-based systems, or mixtures of water and water-miscible non-aqueous solvents. The dispersibility of the composition is in turn determined by the nature of the formulated insecticide active ingredients, namely soluble concentrate, suspension concentrate, microemulsion, water-in-oil emulsion, etc, as well as the nature of the solvent base for the composition, the presence of surfactants and other dispersal aids, as is known in the art.

The composition may optionally be prepared as a concentrated formulation intended for dilution prior to use or may be prepared as a ready-to-use product.

The composition may optionally be formulated to produce a delivery system that is suitable for wood or wood products in a moist or dry state.

The method of the invention involves surface treatment of timber or wood products using insecticidally effective amounts of the composition described above. The composition may be applied to the surface of timber or wood products by spraying, dipping, painting, brushing, pouring, rolling, curtain coating, hot or cold soaking, partial vacuum, misting, or a combination thereof.

The method of the invention is further characterised in that no part of the one or more new, untreated surfaces is more than 50 mm from any neighbouring treated surface, and/or the combined area of the one or more new, untreated surfaces comprises less than 33% of the total surface area of the timber or wood product.

The untreated surfaces will most commonly be exposed by post treatment operations such as sawing, cutting, drilling, planing, gauging, sanding, chamfering, beveling, producing punch outs for electrical cables etc. However, it should be noted that the untreated surfaces referred to in this disclosure may also be the result of the primary surface treatment operation itself, for example, the ends of pieces of timber missed by a linear sprayer.

Preferably the method of the invention produces a minimum insecticide penetration of 0-10 mm below the treated surfaces of timber or wood products.

More preferably the method of the invention produces a minimum insecticide penetration of 0-5 mm below the treated surfaces of timber or wood products.

As used in this disclosure, the term "insecticidally effective amount" is used to indicate a concentration or product loading at which the non-repellent insecticide provides acceptable protection of the surface-treated timber or wood product in a standardised test method. For example, concentrations or product loadings may be expressed in terms of grams of active ingredient per cubic metre (gai/m$^3$) or grams of active ingredient per square metre (gai/m$^2$). Alternatively concentrations may be expressed on a mass basis as % m/m (mass of insecticide/mass of timber or wood product). What is considered "acceptable" protection varies from one test method to another. For example, sample pieces of untreated timber and surface-treated timber at different product loadings subjected to a termite trial are weighed before and after a 3 to 6 month exposure to termites to determine the mass loss of the samples resulting from termite attack. An average mass loss of less than 5% for a set of treated samples may be considered an acceptable level of protection in a trial where the average mass loss of the untreated samples is greater than 30-50%.

Timber or wood products suitable for the method of this invention generally refer, but are not limited, to cellulosic substrates including sawn timber or lumber, logs, posts, engineered wood products including glued solid timber, glued laminated timber, laminated veneer lumber (LVL), plywood, and reconstituted wood products including strand board, oriented strand board, flake board, particle board, medium density fibreboard, high density fibreboard, hardboard and combination products. Throughout the disclosure and claims when reference is made to the terms timber, or wood, or wood products that reference includes all of the above.

The timber or wood product to be surface-treated may be moist or dry. Generally dry timber or wood products are better able to absorb surface treatment compositions than those in a wet or moist state. Additionally the timber or wood products to be surface-treated may be at ambient temperature, or may be in a pre-heated state, such as timber taken from a drying kiln, and engineered wood products or reconstituted wood products after hot pressing. As is known in the art timber or wood products tend to absorb superficially applied liquids to a greater degree hot than cold.

BRIEF DESCRIPTION OF THE DRAWING

The invention is now further described by way of example only, with reference to FIG. 1, which comprises photograph of untreated and treated timber after termite exposure.

The examples and the particular proportions set forth are intended to be illustrative only and are thus non-limiting.

EXAMPLE 1

Imidacloprid Suspension Concentrate

| Component | Grams/litre |
| --- | --- |
| Imidacloprid | 30.0 |
| Magnesium aluminium silicate | 6.0 |
| Morwet D-450 | 10.0 |
| Gensil 2000 | 0.1 |
| Benzisothiazolin-3-one | 1.0 |
| Xanthan gum | 2.0 |

Prepare a slurry of magnesium aluminum silicate by high shear mixing in water. Mix in Morewet D-450, imidacloprid and Gensil 2000, mill the mixture to achieve the desired particle size, then combine with a pre-prepared xanthan gum slurry in water, add benzisothiazolin-3-one preservative and make up to volume with water.

EXAMPLE 2

Ready-To-Use Imidacloprid Soluble Concentrate

| Component | Grams/litre |
|---|---|
| Imidacloprid | 2.75 |
| N-Methyl pyrrolidone | 37.5 |
| Break-Thru OE 441 | 6.3 |
| Methyl oleate 117 | 857.2 |

Dissolve imidacloprid in warm N-methyl pyrrolidone and add Break-Thru OE441 then methyl oleate.

EXAMPLE 3

Thiacloprid Suspension Concentrate

| Component | Grams/litre |
|---|---|
| Thiacloprid | 30.0 |
| Magnesium aluminium silicate | 6.0 |
| Morwet D-450 | 10.0 |
| Gensil 2000 | 0.1 |
| Benzisothiazolin-3-one | 1.0 |
| Xanthan gum | 2.0 |

Prepare a slurry of magnesium aluminum silicate by high shear mixing in water. Mix in Morewet D-450, thiacloprid and Gensil 2000, mill the mixture to achieve the desired particle size, then combine with a pre-prepared xanthan gum slurry in water, add benzisothiazolin-3-one preservative and make up to volume with water.

EXAMPLE 4

Thiacloprid Emulsifiable Concentrate

| Component | Grams/kg |
|---|---|
| Thiacloprid | 30 |
| N-Methyl pyrrolidone | 870 |
| Teric 200 | 100 |

Dissolve thiacloprid in N-Methyl pyrrolidone and add molten Teric 200 with stirring.

EXAMPLE 5

Dinotefuran Soluble Concentrate

| Component | Grams/litre |
|---|---|
| Dinotefuran | 30.0 |
| Teric N9 | 10.0 |
| Gensil 2000 | 0.1 |
| Benzisothiazolin-3-one | 1.0 |

Dissolve dinotefuran in water and mix in remaining components.

EXAMPLE 6

Clothianidin Suspension Concentrate

| Component | Grams/litre |
|---|---|
| Clothianidin | 30.0 |
| Magnesium aluminium silicate | 6.0 |
| Morwet D-450 | 10.0 |
| Gensil 2000 | 0.1 |
| Benzisothiazolin-3-one | 1.0 |
| Xanthan gum | 2.0 |

Prepare a slurry of magnesium aluminum silicate by high shear mixing in water. Mix in Morewet D-450, clothianidin and Gensil 2000, mill the mixture to achieve the desired particle size, then combine with a pre-prepared xanthan gum slurry in water, add benzisothiazolin-3-one preservative and make up to volume with water.

EXAMPLE 7

Nitenpyram Soluble Concentrate

| Component | Grams/litre |
|---|---|
| Nitenpyram | 30.0 |
| Teric N9 | 10.0 |
| Gensil 2000 | 0.1 |
| Benzisothiazolin-3-one | 1.0 |

Dissolve nitenpyram in water and mix in remaining components.

EXAMPLE 8

Fipronil Suspension Concentrate

| Component | Grams/litre |
|---|---|
| Fipronil | 200.0 |
| Methylchloroisothiazolinone | 0.2 |
| Benzisothiazolin-3-one | 0.3 |
| Gensil 2000 | 0.5 |
| Propylene glycol | 49.0 |
| Magnesium aluminium silicate | 6.8 |
| Soprophor FL | 35.0 |
| Antarox B/848 | 12.0 |
| Citric acid | 0.3 |
| Sodium hydroxide | 0.1 |
| Xanthan gum | 2.0 |

Prepare a slurry of magnesium aluminum silicate by high shear mixing in water. Mix in Soprophor FL, Antarox B/848, propylene glycol, fipronil and Gensil 2000, mill the mixture to achieve the desired particle size, then combine with a pre-prepared xanthan gum slurry in water, add benzisothiazolin-3-one and methylchloroisothiazolinone preservatives, citric acid and sodium hydroxide and make up to volume with water.

EXAMPLE 9

Chlorfenapyr Emulsifiable Concentrate

| Component | Grams/litre |
|---|---|
| Chlorfenapyr | 100.0 |
| Aromatic 150 | 719.2 |
| Sponto ME 402 | 120.0 |

Dissolve chlorfenapyr into Aromatic 150 and add Sponto ME 402 with stirring.

EXAMPLE 10

Indoxacarb Suspension Concentrate

| Component | Grams/litre |
|---|---|
| Indoxacarb | 125.0 |
| Benzisothiazolin-3-one | 0.4 |
| Gensil 2000 | 0.6 |
| Diethylene glycol | 30.0 |
| Magnesium aluminium silicate | 5.0 |
| Soprophor FL | 25.0 |
| Citric acid | 0.8 |
| Xanthan gum | 1.8 |

Prepare a slurry of magnesium aluminum silicate by high shear mixing in water. Mix in Soprophor FL, diethylene glycol, indoxacarb and Gensil 2000, mill the mixture to achieve the desired particle size, then combine with a pre-prepared xanthan gum slurry in water, add benzisothiazolin-3-one preservative and citric acid and make up to volume with water.

EXAMPLE 11

Termite Resistance of Timber Treated by Superficial Application of Insecticides in Water

*Pinus radiata* timber was sprayed with imidacloprid (non-repellent insecticide) or bifenthrin (repellent insecticide) dried, weathered, cut into short lengths to expose two untreated surfaces at each end and exposed to termites to determine treatment efficacy. Timber treatments and testing were conducted according to the H2F (surface sprayed) protocols of the Australasian Wood Preservation Committee (AWPC). Gauged, knot free timber (140 mm×45 mm) was cut into 600 mm lengths (4 per treatment rate) and sprayed at 150 ml/m$^2$ as described in Table 1. After spraying all pieces were block stacked for six hours to maximise penetration, left standing on their ends to dry for 3 days, then placed outside for 4 weeks to provide UV exposure and weathering. Finally the pieces were sawn into 70 mm lengths, vacuum dried at −90 kPa and 40° C. for 5 days, then weighed. The untreated freshly sawn areas represent 32.7% of the total (untreated+treated) area of the blocks.

TABLE 1

Summary of aqueous insecticide treatments.

| Insecticide treatment | Product loading (superficial) | Product loading (volumetric) |
|---|---|---|
| Untreated | — | — |
| Imidacloprid + Abzorbe | 0.085 gai/m$^2$ | 5.0 gai/m$^3$ |
| Imidacloprid + Abzorbe | 0.170 gai/m$^2$ | 10.0 gai/m$^3$ |
| Imidacloprid + Abzorbe | 0.341 gai/m$^2$ | 20.0 gai/m$^3$ |
| Bifenthrin + Abzorbe | 0.187 gai/m$^2$ | 10.9 gai/m$^3$ |
| Abzorbe (solvent control) | — | — |

Treatments containing imidacloprid were dilutions of a 30 grams/litre imidacloprid suspension concentrate (Permatek IM 30®) in water. The bifenthrin treatment was a dilution of a 100 grams/litre emulsifiable concentrate of bifenthrin. Abzorbe® is a polyether trisiloxane surfactant used at 0.08% (v/v).

Two termite trials were conducted at Alice River, Townsville, Australia, with six replicates per trial. Each replicate contained one piece from each of the six treatments in Table 1, packed in a 3×2 arrangement in a plastic lunch box with one of the 140 mm×45 mm freshly sawn, untreated surfaces facing uppermost. Four pieces of untreated *P. radiata* bait wood were also included in each box. Lunch boxes were positioned next to active *Coptotermes acinaciformis* termite mounds in the manner specified by AWPC. After 119 days the lunch boxes were lifted and each test piece was assessed visually for superficial termite damage. In addition pieces were washed, oven dried, then reweighed to assess mass losses resulting from termite damage. The data analysed by analysis of variance (ANOVA) using Duncan's New Multiple-Range Test for significance are summarised in Tables 2 and 3. A photograph of one replicate from Trial 2072 is shown in FIG. 1.

TABLE 2

ANOVA means from Termite Trial 2071.

| Insecticide treatment | Mass loss | Damage (visual assessment) |
|---|---|---|
| Untreated | a. 67.10% a | b. 73.33% a |
| Imidacloprid 5.0 gai/m3 | a. 8.06% bc | b. 14.00% bc |
| Imidacloprid 10.0 gai/m3 | a. 0.00% c | b. 0.50% c |
| Imidacloprid 20.0 gai/m3 | a. 0.01% c | b. 0.08% c |
| Bifenthrin 10.9 gai/m3 | a. 10.96% bc | b. 19.50% bc |
| Solvent control | a. 32.51% b | b. 33.00% b |

Means followed by same letter do not significantly differ (P = .05, Duncan's New MRT).

TABLE 3

ANOVA means from Termite Trial 2072.

| Insecticide treatment | Mass loss | Damage (visual assessment) |
|---|---|---|
| Untreated | a. 72.92% a | b. 76.25% a |
| Imidacloprid 5.0 gai/m3 | a. 0.88% b | b. 2.08% b |

TABLE 3-continued

ANOVA means from Termite Trial 2072.

| Insecticide treatment | Mass loss | Damage (visual assessment) |
|---|---|---|
| Imidacloprid 10.0 gai/m3 | a. 1.79% b | b. 2.75% b |
| Imidacloprid 20.0 gai/m3 | a. 0.01% b | b. 0.33% b |
| Bifenthrin 10.9 gai/m3 | a. 5.07% b | b. 8.33% b |
| Solvent control | a. 68.33% a | b. 72.50% a |

Means followed by same letter do not significantly differ (P = .05, Duncan's New MRT).

Termites damaged untreated timber severely, with complete consumption of the blocks in some replicates (e.g. see FIG. 1 where only the aluminum identification tag remained), and an average of 67-73% average mass loss in the two trials (Tables 2 and 3). Timber treated with the solvent control (Abzorbe in water) suffered a similar fate. Imidacloprid applied superficially at 5.0 grams/m$^3$ provided partial termite protection in Trial 2071(8% average mass loss) and good protection in Trial 2072 (0.9% average mass loss). At 10 and 20 grams/m$^3$ imidacloprid applied superficially provided consistently good protection in both trials with average mass losses were well below the 5% threshold deemed to be acceptable for this trial method. Bifenthrin applied at 10.9 grams/m$^3$ provided moderate protection in these trials. Visual assessments provided essentially equivalent data in both trials.

EXAMPLE 12

Termite Resistance of Timber Treated by Superficial Application of Insecticides in a Non-Aqueous Solvent Gauged, kiln dried *Pinus radiata* timber (90 mm×40 mm) was cut into 500 mm lengths and sprayed at 50 ml/m$^2$ with solvent based treatment solutions as described in Table 2. After spraying all pieces were dried for two hours then sawn into 50 mm lengths, vacuum dried at −90 kPa and 40° C. for 5 days, then weighed. The untreated freshly sawn areas represent 35.6% of the total (untreated+treated) area of the blocks. One set of blocks was also end treated (0.014 gai/m$^2$ imidacloprid) after sawing and before vacuum drying.

TABLE 4

Summary of non-aqueous insecticide treatments.

| Insecticide treatment | Treated area | Product loading (superficial) | Product loading (volumetric) |
|---|---|---|---|
| Untreated | — | — | — |
| Solvent control | Surface | — | — |
| Imidacloprid | Surface | 0.00014 gai/m$^2$ | 0.010 gai/m$^2$ |
| Imidacloprid | Surface | 0.0014 gai/m$^2$ | 0.10 gai/m$^2$ |
| Imidacloprid | Surface | 0.014 gai/m$^2$ | 1.0 gai/m$^2$ |
| Imidacloprid | Surface + cut ends | 0.014 gai/m$^2$ | 1.6 gai/m$^2$ |
| Imidacloprid | Surface | 0.14 gai/m$^2$ | 10 gai/m$^2$ |
| Bifenthrin | Surface | 1.4 gai/m$^2$ | 100 gai/m$^2$ |
| Untreated | — | — | — |

The imidacloprid treatment solution used to produce the 10 gai/m$^3$ volumetric loading is shown in Example 2. The remaining imidacloprid treatment solutions, and the solvent control, contained the same ingredients with varying imidacloprid concentrations. The bifenthrin treatment solution was a 3.6-fold dilution in methyl oleate of a 100 grams/litre emulsifiable concentrate of bifenthrin.

A termite trial was conducted (202 days exposure) as described in Example 8. Termites severely damaged untreated timber as well as timber treated with solvent and low rates of imidacloprid (Table 5). Imidacloprid provided good control at 1-10 gai/m$^3$ regardless of whether or not untreated ends exposed by cutting after the initial treatment were re-treated with the insecticide. Bifenthrin, a repellent insecticide used as a control, provided excellent protection at 100 gai/m$^3$.

TABLE 5

ANOVA means from Termite Trial 1589.

| Insecticide treatment | Mass loss | Damage (visual assessment) |
|---|---|---|
| Untreated | 87.23% a | 84.17% a |
| Solvent control | 97.15% a | 93.17% a |
| Imidacloprid 0.010 gai/m3 | 77.81% ab | 83.17% a |
| Imidacloprid 0.10 gai/m3 | 55.27% b | 56.67% b |
| Imidacloprid 1.0 gai/m3 | 3.21% c | 5.00% c |
| Imidacloprid 1.6 gai/m3 Surface + cut ends | 3.39% c | 0.00% c |
| Imidacloprid 10 gai/m3 | 1.93% c | 4.17% c |
| Bifenthrin 100 gai/m3 | 0.72% c | 0.00% c |
| Untreated | 97.13% a | 96.33% a |

Means followed by same letter do not significantly differ (P = .05, Duncan's New MRT).

Having generally described this invention, including the best mode thereof, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein.

Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

The Invention may also broadly be said to consist in the parts, elements and features referred or indicated in the specification, individually or collectively, and any or all combinations of any of two or more parts, elements, members or features and where specific integers are mentioned herein which have known equivalents such equivalents are deemed to be incorporated herein as if individually set forth.

Throughout the description and claims of the specification the word "comprise" or variations thereof are not intended to exclude other additives, components or steps.

Kit of Parts

It will also be understood that where a product, method or process as herein described or claimed and that is sold incomplete, as individual components, or as a "Kit of Parts", that such exploitation will also fall within the ambit of the invention.

In a preferred embodiment the invention includes within its scope a kit of parts, the kit of parts providing for a wood protectant composition for surface treatment of timber or wood products comprising in separate containers or as separate compartments within the same container:

(A) an insecticidally effective amount of one or more non-repellent insecticides and
(B) one or more penetration aids and optionally
(C) one or more other aforementioned ingredients.

We claim:

1. A wood protectant composition comprising as sole active ingredient an insecticidally effective amount of one or more non-repellent insecticides, selected from non-repellant neonicotinoids, phenylpyrazoles, diamide insecticides, spinosyns, indoxacarb, and a combination thereof, when used in a single, surface treatment for a timber or wood product whereby said composition provides, in a single surface treatment, protection against insect damage to all surfaces without any need for a secondary insecticide treatment of one or more new, untreated surfaces wherein a post-treatment processing operation is performed and whereby the single, surface treatment is characterised in that:
   (i) non-repellent insecticide is surface applied to the timber or wood product at an active ingredient loading of greater than $0.10$ gai/m$^3$, and
   (ii) no part of the one or more new, untreated surfaces resulting from a post-treatment processing operation is more than 50 mm from any neighbouring treated surface, or the combined area of the one or more new, untreated surfaces comprises less than 33% of the total surface area of the timber or wood product.

2. A composition according to claim 1 wherein the one or more non-repellent neonicotinoids is selected from the group comprising imidacloprid, thiacloprid, dinotefuran, clothianidin and nitenpyram.

3. A composition according to claim 2 wherein the non-repellent neonicotinoid comprises imidacloprid.

4. A composition according to claim 1 wherein the one or more phenylpyrazoles is selected from fipronil and ethiprole.

5. A composition according to claim 1 wherein the one or more diamide insecticides is selected from rynaxypyr and flubendiamide.

6. A composition according to claim 1 wherein the one or more spinosyns is selected from spinosad and spinetoram.

7. A composition according to claim 1, further comprising one or more components selected from the group comprising penetration aids, a fungicide, a bactericide, a mouldicide, or an algaecide, insecticidal synergists, pigments, visible or invisible treatment markers, water repellents, fire retardants, solvents, surfactants enabling dispersion into water, non-aqueous solvents and mixtures of water and water-miscible non-aqueous solvents.

8. A composition according claim 7 wherein the one or more components is a fungicide, a bactericide, a mouldicide, or an algaecide.

9. A composition according to claim 7, wherein the one or more penetration aids is a surfactant, wetting agent, oil, alcohol, glycol, glycol ether, ester, amine, alkanolamine, amine oxide, quaternary ammonium compound, triglyceride, fatty acid ester, fatty acid ether, N-methyl pyrrolidone, dimethylformamide, dimethylacetamide, or dimethyl sulfoxide.

10. A composition according to claim 1, providing a minimum insecticide penetration of 0-10 mm, and preferably 0-5 mm, below the treated surface of a timber or wood product.

11. A composition according to claim 1, formulated either as concentrate to be diluted prior to use or as a ready-to-use product.

12. A method for surface treatment of timber or a wood product that provides protection against insect damage to all surfaces without any need for a secondary insecticide treatment of one or more new, untreated surfaces generated by post-treatment processing operations including sawing, cutting, drilling, bevelling, planing, sanding and/or a combination thereof, the method comprising applying to the surface of the timber or wood product, an insecticidally effective amount of a composition according to claim 1; the method being further characterised in that:
   (i) the non-repellent insecticide is surface applied to the timber or wood product at an active ingredient(s) loading of greater than $0.10$ gai/m$^3$, and
   (ii) no part of the one or more new, untreated surfaces resulting from a post-treatment processing operation is more than 50 mm from any neighbouring treated surface, or the combined area of the one or more new, untreated surfaces comprises less than 33% of the total surface area of the timber or wood product.

13. The method according to claim 12 wherein the surface treatment produces a minimum insecticide penetration of 0-10 mm, and preferably 0-5 mm, below the treated surfaces.

14. The method according to claim 12 wherein the timber or wood product is selected from the group comprising: sawn timber, lumber, logs, posts, glued solid timber, glued laminated timber, laminated veneer lumber, plywood, strand board, oriented strand board, flake board, particle board, medium density fibreboard, high density fibreboard, hardboard and a combination product.

15. The method according to claim 12 wherein the composition is applied to the surface of the timber or wood product by spraying, dipping, painting, brushing, pouring, rolling, curtain coating, hot or cold soaking, partial vacuum, misting or a combination thereof.

16. The method according to claim 12 wherein the composition is applied to the surface of the timber or wood product in water or a non-aqueous solvent or a mixture of water and a water-miscible, non-aqueous solvent.

17. The method as claimed in claim 12 wherein the timber or wood product is in a dry or moist state prior to surface treatment and/or wherein the timber or wood product is at ambient temperature or is pre-heated prior to surface treatment.

18. A timber or wood product when derived from a method of claim 12.

* * * * *